United States Patent [19]

Hwan et al.

[11] Patent Number: 5,789,627
[45] Date of Patent: Aug. 4, 1998

[54] METHOD FOR THE PURIFICATION OF TERTIARY BUTYL ALCOHOL AND TO ITS USE IN THE MANUFACTURE OF MTBE

[75] Inventors: Rei-Yu Judy Hwan, Sugarland; Kyle Lee Preston, Port Arthur, both of Tex.

[73] Assignee: Huntsman Specialty Chemicals Corp., Austin, Tex.

[21] Appl. No.: 802,746

[22] Filed: Feb. 20, 1997

[51] Int. Cl.$^6$ .................................................. C07C 41/09
[52] U.S. Cl. .......................... 568/697; 568/698; 568/910
[58] Field of Search .............................. 568/697, 698, 568/910

[56] References Cited

U.S. PATENT DOCUMENTS

| | | | |
|---|---|---|---|
| 4,296,263 | 10/1981 | Worrell et al. | 568/910 |
| 5,243,091 | 9/1993 | Kruse et al. | 568/697 |
| 5,292,964 | 3/1994 | Gupta et al. | 568/697 |
| 5,354,912 | 10/1994 | Hwan et al. | 568/697 |
| 5,637,777 | 6/1997 | Aittamaa et al. | 568/697 |

*Primary Examiner*—Gary Geist
*Assistant Examiner*—S. Padmanabhan
*Attorney, Agent, or Firm*—Russell R. Stolle; Carl G. Ries

[57] ABSTRACT

Methyl tertiary butyl ether is prepared from contaminated tertiary butyl alcohol and methanol by decomposing peroxides in a peroxides decomposition reactor, by dehydrating the tertiary butyl alcohol to form isobutylene and also decomposing acidic contaminants in a tertiary butyl alcohol dehydration reactor to form a feedstock that is distilled to provide a first lower boiling fraction comprising isobutylene and water; from which isobutylene is recovered for reaction with methanol in an etherification reactor containing a bed of an etherification catalyst to form methyl tertiary butyl ether.

16 Claims, 1 Drawing Sheet

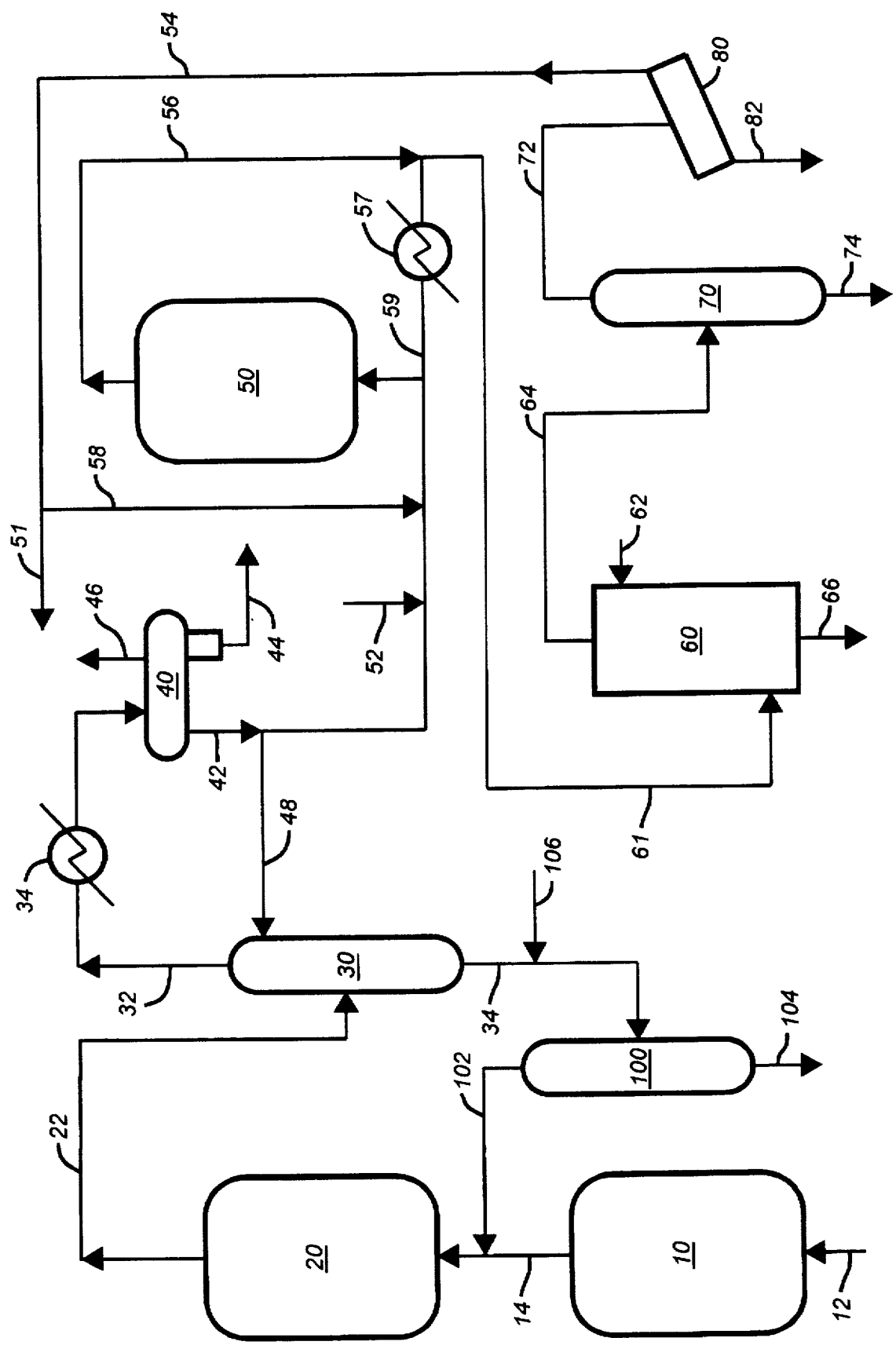

METHOD FOR THE PURIFICATION OF TERTIARY BUTYL ALCOHOL AND TO ITS USE IN THE MANUFACTURE OF MTBE

BACKGROUND OF THE INVENTION

1. Technical Field of the Invention

This invention relates to the purification of tertiary butyl alcohol and to its use in the manufacture of methyl tertiary butyl ether. More particularly, this invention relates to a method for the substantially complete removal from the tertiary butyl alcohol of oxygen-containing impurities, including peroxide contaminants and acidic contaminants such as tertiary butyl formate, to the dehydration of the tertiary butyl alcohol to form isobutylene and to the reaction of the isobutylene with methanol to manufacture methyl tertiary butyl ether.

Methyl tertiary butyl ether is useful as a blending component in high octane gasoline.

2. Prior Art

Worrell U.S. Pat. No. 4,296,263 discloses the oxidation of isobutane with air to provide to tertiary butyl alcohol and tertiary butyl hydroperoxide. It is disclosed that the reaction product, a solution of tertiary butyl hydroperoxide in tertiary butyl alcohol, contains minor amounts of oxygen-containing by-products such as acetic acid, formic acid and esters thereof that are purged from the system during purification of the reaction product.

The tertiary butyl hydroperoxide in the solution of tertiary butyl hydroperoxide in tertiary butyl alcohol can be decomposed thermally or catalytically to form additional tertiary butyl alcohol.

A number of catalysts have been proposed for this purpose, such as cobalt borate as disclosed in U.S. Pat. No. 4,547,598, a metal phthalocyanine catalyst as disclosed in Sanderson et al. U.S. Pat. No. 4,910,349, an imidazole-promoted methyl metal phthalocyanine catalyst as disclosed in Sanderson et al. U.S. Pat. No. 4,912,266, a base promoted metal phthalocyanine catalyst as disclosed in Sanderson et al. U.S. Pat. No. 4,912,267, a solid ruthenium catalyst as disclosed in Sanderson et al. U.S. Pat. No. 4,922,033, a promoted metal porphine catalyst as disclosed in Sanderson et al. U.S. Pat. No. 4,922,034, etc.

The tertiary butyl alcohol charge stock derived from tertiary butyl hydroperoxide in this manner will be contaminated with oxygen-containing impurities.

Processes for the manufacture of methyl tertiary butyl ether from tertiary butyl alcohol and methanol are known, as illustrated, for example, by Kruse et al. U.S. Pat. No. 5,243,091, Gupta U.S. Pat. No. 5,292,964, Hwan et al. U.S. Pat. No. 5,354,912, Kruse et al. U.S. Pat. No. 5,386,065, Kruse et al. U.S. Pat. No. 5,387,721 and Cassata et al. U.S. Pat. No. 5,395,982. In the practice of these processes, the tertiary butyl alcohol feedstock is passed through a peroxides decomposition reactor before being charged to an etherification reactor together with methanol for the formation of methyl tertiary butyl ether.

For example, Kruse et al. U.S. Pat. No. 5,243,091 discloses a method for the preparation of methyl tertiary butyl ether wherein the tertiary butyl alcohol is initially charged to a peroxides decomposition zone, which is preferably a thermal decomposition zone. The peroxides in the contaminated tertiary butyl alcohol feedstock are decomposed at a temperature of about 100° to about 200° C., a pressure of about 80 to about 500 psia at a flow rate of about 0.5 to 20 volumes of feedstock per reactor volume per hour to thereby provide a substantially peroxides-free tertiary butyl alcohol reaction product. The thus-treated tertiary butyl alcohol, which will still contain oxygen-containing impurities such as tertiary butyl formate, is then mixed with methanol and the mixture is catalytically reacted to form an etherification reaction product comprising unreacted methanol, unreacted tertiary butyl alcohol, water, isobutylene, methyl tertiary butyl ether, and oxygen-containing impurities present in the tertiary butyl alcohol feedstock. Methyl tertiary butyl ether is recovered from the reaction mixture.

Sanderson et al. U.S. Pat. No. 5,354,917 discloses a method wherein an isobutane oxidation product comprising a solution of 5 to 30 wt. % of tertiary butyl hydroperoxide in tertiary butyl alcohol is brought into contact with a catalyst consisting of alumina or carbon having rhodium deposited thereon in order to convert the tertiary butyl hydroperoxide to decomposition products, principally tertiary butyl alcohol. Sanderson et al. specify reaction conditions including a temperature of about 25° to about 250° C. and a pressure of about 0 to 1000 psig, with a temperature of about 40° to about 150° C. and a pressure of about 0 psig being preferred. Tertiary butyl alcohol is recovered from the decomposition products but will be contaminated with minor amounts of oxygen-containing impurities including peroxides and formates.

A variety of other catalysts may be used to treat a tertiary butyl alcohol feedstock contaminated with peroxide impurities, such as a nickel, copper, chromia catalyst as disclosed in Sanderson et al. U.S. Pat. No. 4,704,482, an iron, copper, chromia, cobalt catalyst as disclosed in Sanderson et al. U.S. Pat. No. 4,705,903, a base treated hydrogenation catalyst from groups VIB or VIIIB of the Periodic Table as disclosed in Sanderson et al. U.S. Pat. No. 4,742,179, a nickel, copper, chromium and barium catalyst as disclosed in Sanderson et al. U.S. Pat. No. 4,873,380, etc.

Another process for the manufacture of methyl tertiary butyl ether is disclosed in copending Preston et al. application Ser. No. 08/345,663, filed Nov. 28, 1994, and entitled "Sequential Reaction of TBA and Isobutylene with Methanol" wherein a tertiary butyl alcohol feedstock contaminated with peroxides is passed through a peroxides decomposition reactor and then reacted with methanol in an etherification reactor to form an etherification reaction product that is distilled to provide a lower boiling fraction comprising methanol, methyl tertiary butyl ether and isobutylene that is water-washed for the removal of methanol and to form a raffinate that is distilled to form a higher boiling methyl tertiary butyl ether product and a lower boiling fraction from which isobutylene is recovered for reaction with methanol in a secondary reactor.

SUMMARY OF THE INVENTION

When tertiary butyl alcohol is prepared by the oxidation of isobutane and/or tertiary butyl hydroperoxide the tertiary butyl alcohol reaction product will contain minor amounts of contaminants such as tertiary butyl hydroperoxide, ditertiary butyl peroxide, allyl tertiary butyl peroxide, etc., and will also contain minor amounts of oxygen-containing contaminants including acetone, isopropyl alcohol, etc., and acidic by-products such as acetic acid, formic acid and esters thereof, including methyl formate and tertiary butyl formate, and tertiary butyl acetate. The contaminated tertiary butyl alcohol charge stock prepared in this fashion is conventionally passed through a peroxides decomposition reactor to prepare a tertiary butyl alcohol feedstock that is fed to a methyl tertiary butyl ether etherification reactor together with methanol to provide the methyl tertiary butyl ether etherification product substantially free from peroxide impurities. The thus-treated tertiary butyl alcohol will still contain a minor amount of oxygen-containing impurities, such as acetone, isopropyl alcohol and also formate esters such as tertiary butyl formate and tertiary butyl acetate. Tertiary butyl formate is a refractory ester and is removed only with extreme difficulty. However, during the reaction of tertiary butyl alcohol with methanol to form a reaction product containing methyl tertiary butyl ether and during the work-up of the reaction product, the oxygen-containing impurities, and especially the formate esters can decompose and react with methanol to form volatile by-products including corrosive acid precursors such as methyl formate and methyl acetate, thus creating a severe corrosion problem in the downstream equipment.

These and other related problems are resolved through the process of the present invention wherein:

a) contaminated tertiary butyl alcohol charge containing from about 0.5 to about 5 wt. % of oxygen-containing impurities, including peroxides such as tertiary butyl hydroperoxide, ditertiary butyl peroxide, allyl hydroperoxide and acidic by-products such as acetone, t-butyl formate, isopropyl alcohol, etc., is charged to a peroxides decomposition reactor to prepare a tertiary butyl alcohol charge stock that will typically comprise about 95 to about 99 wt. % of tertiary butyl alcohol and less than about 0.1 wt. % of peroxide contaminants but will typically contain from about 0.1 to about 1 wt. % of acidic by-products;

b) the tertiary butyl alcohol charge stock is charged to a tertiary butyl alcohol dehydration reactor to form an isobutylene dehydration product by dehydrating tertiary butyl alcohol to form isobutylene and water and to decompose residual hydroperoxide and ester impurities;

c) the isobutylene dehydration product is charged to a first distillation column and separating it therein into a first higher boiling fraction comprising tertiary butyl alcohol and water and a first lower boiling fraction comprising isobutylene and water; and d) isobutylene is recovered from the first lower boiling fraction for reaction with methanol in a methyl tertiary butyl ether etherification reactor to form a methyl tertiary butyl ether etherification reaction product from which methyl tertiary butyl ether can be recovered.

DESCRIPTION OF PREFERRED EMBODIMENTS

In accordance with a preferred embodiment of the present invention, a method for the continuous preparation of methyl tertiary butyl ether (MTBE) from tertiary butyl alcohol (TBA) and methanol (MeOH) is provided comprising the steps of:

a) continuously charging tertiary butyl alcohol contaminated with from about 0.5 to about 5 wt. % of oxygen-containing impurities, including peroxides such as tertiary butyl hydroperoxide, ditertiary butyl peroxide, allyl hydroperoxide and acidic by-products such as acetone, t-butyl formate, t-butyl acetate, isopropyl alcohol, etc., to a thermal peroxides decomposition reactor and thermally decomposing the peroxide contaminants therein to provide a tertiary butyl alcohol charge stock that will typically comprise about 95 to about 99 wt. % of tertiary butyl alcohol and less than about 0.1 wt. % of peroxide contaminants but will typically contain from about 0.1 to about 1 wt. % of acid precursors including formates and acetates, b) continuously charging the tertiary butyl alcohol charge stock to a tertiary butyl alcohol dehydration reactor containing a tertiary butyl alcohol dehydration catalyst and dehydrating tertiary butyl alcohol to form isobutylene and water and to completely decompose the oxygen-containing acidic contaminants therein to form a non-corrosive feedstock comprising tertiary butyl alcohol, isobutylene and water that is substantially completely free from peroxide and formate contaminants, c) continuously charging the feedstock to a first distillation zone and separating it therein into a first lower boiling distillation fraction comprising isobutylene and water and a first higher boiling distillation fraction comprising tertiary butyl alcohol and water, d) continuously recovering isobutylene from the first lower boiling distillation fraction, e) continuously charging a reaction feed mixture comprising methanol and recovered isobutylene to an etherification reactor containing a bed of an etherification catalyst and reacting said reaction feed mixture therein to form a non-corrosive etherification reaction product comprising methanol, isobutylene, methyl tertiary butyl ether and water, f) continuously charging the etherification reaction product to a methanol solvent extraction zone and contacting the etherification reacting product therein with water to provide an overhead extract comprising isobutylene, water and methyl tertiary butyl ether, and a raffinate comprising methyl tertiary butyl ether, methanol, and water, and g) continuously charging the extract to a second distillation column and separating it therein into a second lower boiling distillation fraction comprising isobutylene and water and a second higher boiling distillation fraction comprising methyl tertiary butyl alcohol.

Another preferred embodiment of the present invention includes the additional steps of:

h) continuously recovering isobutylene from the second higher boiling distillation, i) continuously recycling the recovered isobutylene to the etherification reactor, j) continuously charging the first higher boiling distillation fraction charged to a third tertiary butyl alcohol recovery distillation zone and separating it therein into a third lower boiling tertiary butyl alcohol recycle fraction and a third higher boiling water fraction, and k) continuously recycling the third lower boiling tertiary butyl alcohol fraction to the dehydration-decomposition reactor.

DETAILED DESCRIPTION OF THE PRESENT INVENTION

Peroxide Decomposition

It is known to prepare tertiary butyl alcohol by the thermal decomposition of tertiary butyl hydroperoxide. It is also known to prepare tertiary butyl alcohol by the catalytic reaction of tertiary butyl hydroperoxide with propylene to form propylene oxide and tertiary butyl alcohol. A tertiary butyl alcohol charge stock derived from tertiary butyl hydroperoxide in this manner will be contaminated with oxygen-containing impurities and typically will contain from about 95 to 98 wt. % of tertiary butyl alcohol and about 2 to about 5 wt. % of oxygen-containing contaminants including tertiary butyl hydroperoxide, ditertiary butyl peroxide, acetone, methyl formate, tertiary butyl formate, isopropyl alcohol, dimethyl ether, etc.

In accordance with the present invention tertiary butyl alcohol containing oxygen-containing acidic contaminants and peroxide contaminants is fed to a thermal peroxides decomposition reactor. The peroxides-contaminated tertiary butyl alcohol is suitably passed through the thermal decomposition reactor at a temperature of about 100° to about 200° C., a pressure of about 80 to about 500 psia at a flow rate of about 0.5 to 20 volumes of feedstock per reactor volume per hour to thereby provide a reaction product containing acidic contaminants and comprising the substantially peroxides-free tertiary butyl alcohol feedstock. The peroxide contaminants will be decomposed to form water and tertiary butyl alcohol, and trace amounts of other decomposition products such as acetone and methyl formate but contaminating quantities of acidic by-products will still be present.

Tertiary Butyl Alcohol Dehydration and Formate Decomposition

In accordance with the present invention, the tertiary butyl alcohol charge stock is fed to a tertiary butyl alcohol dehydration reactor containing a bed of a suitable dehydration catalyst where tertiary butyl alcohol is dehydrated to form isobutylene and water and where the acidic contaminants are substantially completely catalytically decomposed. Reaction conditions to be used include a temperature of about 160° to about 240° C., a pressure of about 80 to about 500 psia at a flow rate of about 0.5 to 20 volumes of charge stock per reactor volume per hour to thereby provide a tertiary butyl alcohol feedstock substantially completely free from oxygen-containing impurities.

The effluent from the tertiary butyl alcohol reactor will typically comprise about 95 to about 99 wt. % of a mixture of tertiary butyl alcohol with isobutylene and will contain less than about 0.1 wt. % of oxygen-containing contaminants.

The Dehydration-Decomposition Catalyst

A wide variety of tertiary butyl alcohol dehydration catalysts can be used, including alumino-silicate zeolites and clays such as, for example, beta-type zeolites, fluoride-treated beta zeolite catalysts, fluoride-treated clay catalysts, etc. A preferred catalyst is a HF treated beta zeolite catalyst.

Zeolites are disclosed in Japanese Patent 0007432 and aluminosilicate zeolites as disclosed in Chang et al. U.S. Pat. No. 4,058,576 may also be used.

Another suitable catalyst is a supported rhodium catalyst consisting essentially of alumina or carbon having about 0.01 to about 1 wt. % of rhodium deposited thereon.

The reaction conditions to be utilized when dehydrating tertiary butyl alcohol in the presence of a tertiary butyl alcohol dehydration catalyst include a temperature of about 160° to about 240° C., a pressure of about 80 to about 500 psia at a flow rate of about 0.5 to 20 volumes of charge stock per reactor volume per hour.

The Etherification Reaction Catalyst

In accordance with the MTBE manufacture and purification method of the present invention, an etherification reactor containing a bed of etherification catalyst is utilized.

Any suitable solid resin etherification catalyst may be used for this purpose, such as a strongly acidic ion exchange resin consisting essentially of sulfonated polystyrene, such as a divinyl benzene crosslinked polystyrene matrix containing from about 0.5 to about 20% of copolymerized divinyl benzene. Resins of this nature are manufactured and sold commercially under various trade names such as "Dowex 50", "Nalcite HCR" and "Amberlyst 15". The use of catalyst of this nature is disclosed, for example, in Rao U.S. Pat. No. 4,144,138.

Also, Kieselguhr impregnated with phosphoric acid as disclosed in Frolich U.S. Pat. No. 2,282,469, titania having phosphoric acid impregnated thereon as disclosed in Knifton U.S. Pat. No. 4,822,921, a hetero polyacid such as 12-tungstophosphoric acid or 12-molybdophosphoric acid supported on titania, etc., may be used.

Reaction conditions to be used include, for example, a temperature of about 35° to about 130° C., and more preferably from about 40° to about 90° C., a pressure of about 50 to about 500 psia, and more preferably from about 150 to about 250 psia, and a contact time of about 0.5 to about 4 volumes of feed per volume of solid resin etherification catalyst per hour. As a consequence, a portion of the methanol and isobutylene will be converted to methyl tertiary butyl ether. Typically, the conversion will amount to about 20 to about 85 wt. %, based on the isobutylene.

BRIEF DESCRIPTION OF THE DRAWING

The drawing is a schematic flow sheet with conventional parts omitted showing the general reaction and recovery sequence of the present invention for the manufacture and purification of methyl tertiary butyl ether.

DESCRIPTION OF THE PREFERRED EMBODIMENT

Turning now to the drawing, there is shown a schematic flow sheet illustrating the preferred method for the practice of the process of the present invention. In the drawing, conventional parts, such as valves, pumps, temperature control sensors, pressure sensors, heaters, coolers, flow control regulation apparatus, reflux condenses, reboilers, etc., have been omitted.

Tertiary butyl alcohol which is contaminated with oxygen-containing impurities including peroxides and acidic contaminants is initially charged by way of a tertiary butyl alcohol charge line 12 to a thermal peroxides decomposition reactor 10 which is operated under thermal peroxide decomposition conditions including a temperature of about 100° to about 200° C., a pressure of about 80 to about 500 psia at a flow rate of about 0.5 to 20 volumes of feedstock per reactor volume per hour to thereby provide a reaction product containing acidic contaminants and comprising a substantially peroxides-free tertiary butyl alcohol charge stock.

The substantially peroxides-free tertiary butyl alcohol charge stock is discharged from the thermal peroxides decomposition reactor 10 by a line 14 leading to a tertiary butyl alcohol dehydration reactor 20 containing a bed of a suitable dehydration catalyst, such as a HF treated beta zeolite catalyst or a rhodium catalyst supported on alumina or carbon. Within the tertiary butyl alcohol dehydration reactor 20 the tertiary butyl alcohol is dehydrated to form an isobutylene feedstock containing isobutylene and water and the oxygen-containing contaminants are substantially completely catalytically decomposed. Reaction conditions to be used include a temperature of about 160° to about 240° C., a pressure of about 80 to about 500 psia at a flow rate of about 0.5 to 20 volumes of charge stock per reactor volume per hour.

The effluent from the tertiary butyl alcohol dehydration reactor 20 is discharged from the reactor 20 by a line 22 and will typically comprise a non-corrosive reaction product containing about 95 to about 99 wt. % of a mixture of tertiary butyl alcohol with isobutylene, will be substantially completely free from peroxide contaminants and will contain less than about 0.1 wt. % of acidic oxygen-containing contaminants.

The effluent is charged by line 22 to a first distillation column 30 where it is fractionated to form a first lower boiling distillation fraction 32 comprising isobutylene and water and a first higher boiling distillation fraction 34 comprising tertiary butyl alcohol and water. Distillation conditions to be used will suitably include a liquid reflux temperature of about 30° to about 100° C., and more preferably about 40° to about 80° C., a reboiler temperature of about 80° to about 115° C., and more preferably from about 95° to about 105° C., and a pressure of about 15 to about 60 psia. As a consequence, the first lower boiling distillation fraction 32 taken overhead from the distillation zone 30 will comprise substantially all of the isobutylene charged to the first distillation zone 30. The first heavier distillation fraction 34 discharged from the first MTBE distillation zone 34 will comprise tertiary butyl alcohol and water. The first lower boiling fraction 32 is cooled to a temperature of about 30° to about 100° C. in a heat-exchanger 34 and then charged to a separator 40 where it can settle to form an isobutylene phase withdrawn from the separator 40 by way of a line 42. Water is discharged in the separator 40 by way of a water discharge line 44 and is suitably purged from the system. Undissolved gases are discharged from the separator 40 by a vent line 46.

A portion of the isobutylene in line 42 is returned to the first distillation column as reflux by reflux line 48 and the remainder of the isobutylene is charged to an etherification reactor 50 containing a bed of etherification catalyst. Any suitable etherification catalyst may be used such as, for example, a solid resin etherification of the type described above, such as a strongly acidic ion exchange resin consisting essentially of sulfonated polystyrene crosslinked with divinyl benzene (e.g., Dowex 50, Nalcite HCR, Amberlyst 15, etc.). As another example, the catalyst may be a fluorophosphoric acid-on-titania catalyst of the type disclosed in Knifton et al. U.S. Pat. No. 4,822,921 or a heteropoly acid such as 12-tungstophosphoric acid or 12-molybdophosphoric acid supported on an inert support such as titania.

Methanol is also charged to the etherification reactor 50 by a methanol charge line 52. Recycle isobutylene obtained in a manner to be described may also be charged to the etherification reactor 50 by a recycle charge line 58. The flow of methanol and isobutylene to the etherification reactor 50 is regulated so that a molar excess of methanol is present in the line 42 leading to the etherification reactor 50 such as, for example, a molar ratio of about 1.1 to about 3 moles of methanol per mol of isobutylene.

Within the etherification reactor 50, the feed mixture is brought into contact with the bed of an etherification catalyst, such as a sulfonic acid resin etherification catalyst under reaction conditions including a pressure of about 30 to about 500 psia, and more preferably from about 200 to about 300 psia, a temperature of about 30° to about 200° C., and more preferably from about 80° to about 140° C., and still more preferably from about 90° to about 130° C. When the catalyst is a supported phosphorus acid-type catalyst, the reaction temperature may suitably be in the range of about 150° to about 190° C.

Contact time within the etherification reactor is suitably such that about 0.5 to about 20 volumes of feed mixture per volume of etherification catalyst per hour are fed to the etherification reactor 10 and, more preferably from about 1 to about 4 volumes of feed mixture per volume of etherification catalyst per hour.

Within the etherification reactor 50, methanol will exothermically react with the isobutylene to form methyl tertiary butyl ether which will be contained in a reaction product discharged from the etherification reactor 50 by way of a line 56. The isobutylene conversion product that is formed which will typically contain from about 0 to about 10 wt. % of isobutylene, about 75 to about 85 wt. % of methyl tertiary butyl ether and from about 10 to about 15 wt. % of methanol and about 0 to about 2 wt. % of tertiary butyl alcohol.

A portion of the etherification reaction product discharged from the etherification reactor 50 by the line 56 is recycled to the etherification reactor 50 by a recycle line 58 containing a heat exchanger 57 where the reaction product is cooled prior to recycle. The amount of the reaction product that is cooled and recycled will be adjusted so as to provide positive temperature control in the etherification reactor 50.

The remainder of the etherification reaction product 56 is charged to a methanol solvent extraction zone 60 where it is countercurrently contacted with water introduced into the solvent extraction zone 60 by a charge line 62.

Within the methanol solvent extraction zone 60, solvent extraction conditions are established for countercurrent solvent extraction including a ratio of isobutylene to water within the range of about 0.8 to about 1.8 volumes of isobutylene per volume of water per hour, and more preferably a ratio of about 1.0 to about 1.5 volumes of isobutylene per volume of water. Extractive conditions to be established may suitably include a temperature of about 20° to about 60° C., and more preferably from about 30° to about 40° C., and a pressure of about 50 to about 500 psia, and more preferably from about 50 to about 150 psia.

As a consequence, a supernatant extract will be formed which is withdrawn from the methanol solvent extraction zone 60 by line 64. The raffinate is discharged from the solvent extraction zone 60 by way of a bottoms charge line 66 for further processing in any desired manner.

The extract is charged by line 64 to a second distillation column 70 where distillation conditions are established including a liquid reflux temperature of about 30° to about 60° C., and more preferably from about 40° to about 55° C., a reboiler temperature of about 100° to about 140° C., and more preferably from about 125° to about 135° C. and a pressure of about 70 to about 120 psia, and more preferably from about 90 to about 110 psia, to thereby form a second lower boiling distillation fraction 72 and a second higher boiling distillation fraction 74 consisting essentially of product, namely methyl tertiary butyl ether.

The second lower boiling distillation fraction 72 will comprise a mixture of isobutylene and water and is suitably charged to a decantation zone 80 where it can settle to form a supernatant isobutylene phase withdrawn from the decantation zone 80 by way of a line 54. Water is discharged in the decantation zone 80 by way of a water discharge line 82 and is suitably purged from the system. All or a portion of the isobutylene in the line 54 may be recycled to the etherification reactor 50.

The first higher boiling distillation fraction 34 discharged from the first distillation zone 30 in accordance with the present invention is charged to a third tertiary butyl alcohol recovery distillation column 100 where it is fractionated under distillation conditions including a liquid reflux temperature of about 35° to about 170° C., and more preferably about 140° to about 150° C., and a reboiler temperature of about 100° to about 190° C., more preferably about 170° to about 180° C., and at a pressure of about 15 to about 190 psia, and more preferably about 110 to about 160 psia, into a third lower boiling distillation fraction comprising tertiary butyl alcohol and water that is discharged from the third distillation column 100 by a line 102 leading to the charge line 14 for the tertiary butyl alcohol dehydration reactor 20 and a third heavier distillation fraction comprising water that is discharged from the distillation zone 100 by a line 104.

The first higher boiling distillation fraction 34 comprises tertiary butyl alcohol and water and any residual acidic contaminants discharged from the tertiary butyl alcohol dehydration reactor 20 by the line 22.

In accordance with the present invention, an aqueous solution of an alkali such as sodium hydroxide, sodium carbonate, potassium hydroxide, etc., is added to the second distillation fraction 34 by a line 106, the alkaline solution being charged in an amount sufficient to substantially completely neutralize the acidic by-products present in the fraction 34.

By way of recapitulation, trans-esterification reactions with methanol in the MTBE etherification reactor convert heavier esters (t-butyl formate and t-butyl acetate) to smaller and more volatile esters (methyl formate and methyl acetate). These smaller esters are difficult to remove in the separation system and form corrosive acidic by-products such as formic acid and acetic acid under aqueous environmental conditions. The present invention removes methanol from the MTBE etherification reactor so that no volatile methyl formate or methyl acetate will be formed. The heavier esters (t-butyl formate, t-butyl acetate, etc., will decompose to formic acid and acetic acid which can be separated into a heavier boiling distillate fraction 34 in the first distillation zone 30. The acidic stream 34 is then neutralized with caustic introduced by line 106 prior to charging it to the third distillation zone 100. The formate salts (neutralized product) will be removed in the heavier boiling fraction 104 and sent to the waste water stream.

What is claimed is:

1. A method for the continuous preparation of methyl tertiary butyl ether (MTBE) from tertiary butyl alcohol (TBA) and methanol (MeOH) which comprises the steps of:
   a) continuously charging tertiary butyl alcohol contaminated with from about 0.5 to about 5 wt. % of impurities, comprising peroxides and acidic by-products, to a peroxides decomposition reactor and decomposing peroxide contaminants therein to prepare a tertiary butyl alcohol charge stock comprising about 95 to about 99 wt. % of tertiary butyl alcohol, less than about 0.1 wt. % of peroxide contaminants and from about 0.1 to about 1 wt. % of acidic by-products;
   b) continuously charging said charge stock to a tertiary butyl alcohol dehydration reactor, dehydrating tertiary butyl alcohol therein to form isobutylene and water and substantially completely decomposing acidic by-products therein to form a non-corrosive isobutylene feedstock comprising tertiary butyl alcohol and isobutylene that is substantially completely free from peroxide and formate contaminants;
   c) continuously charging said feedstock to a first distillation column and separating it therein into a first higher boiling fraction comprising tertiary butyl alcohol and water and a first lower boiling fraction comprising isobutylene and water;
   d) continuously recovering isobutylene from the first lower boiling fraction;
   e) continuously charging a reaction feed mixture comprising methanol and said recovered isobutylene to an etherification reactor containing a bed of an etherification catalyst and reacting said reaction feed mixture therein to form a non-corrosive etherification reaction product comprising unreacted methanol, water, isobutylene and methyl tertiary butyl ether; and
   f) recovering methyl tertiary butyl ether from said reaction product.

2. A method as in claim 1 including the additional steps of:
   g) continuously charging the etherification reaction product to a methanol solvent extraction zone and contacting the reacting product therein with water to provide an overhead extract comprising isobutylene, water and methyl tertiary butyl ether, and a raffinate comprising methyl tertiary butyl ether, methanol, and water;
   h) continuously charging the extract to a second distillation column and separating it therein into a second lower boiling distillation fraction comprising isobutylene and water and a second higher boiling distillation fraction comprising methyl tertiary butyl ether; and
   i) continuously recovering isobutylene from said second lower boiling distillation fraction and charging said recovered isobutylene to said etherification reactor.

3. A method as in claim 1 including the additional steps of:
   j) continuously charging the first higher boiling distillation fraction to a third tertiary butyl alcohol recovery distillation zone and separating it therein into a third lower boiling tertiary butyl alcohol recycle fraction and a third higher boiling water fraction; and
   k) continuously recycling the third lower boiling tertiary butyl alcohol fraction to the tertiary butyl alcohol dehydration reactor.

4. A method as in claim 1 wherein the reaction conditions in the tertiary butyl alcohol dehydration reactor include a temperature of about 160° to about 240° C., a pressure of about 80 to about 500 psia at a flow rate of about 0.5 to 20 volumes of charge stock per reactor volume per hour.

5. A method as in claim 4 wherein the catalyst in the tertiary butyl alcohol dehydration reactor is a rhodium catalyst comprising an alumina or carbon support having about 0.1 to 1 wt. % of rhodium deposited thereon.

6. A method as in claim 5 wherein the support is alumina.

7. A method as in claim 5 wherein the support is carbon.

8. A method as in claim 4 wherein the catalyst in the tertiary butyl alcohol dehydration reactor is an aluminosilicate zeolites.

9. A method as in claim 4 wherein the catalyst in the tertiary butyl alcohol dehydration reactor is a HF treated beta zeolite catalyst.

10. A method for the continuous preparation of methyl tertiary butyl ether (MTBE) from tertiary butyl alcohol (TBA) and methanol (MeOH) which comprises the steps of:
   a) continuously charging tertiary butyl alcohol contaminated with from about 0.5 to about 5 wt. % of impurities comprising peroxides and acidic by-products, to a peroxides decomposition reactor operated under thermal peroxide decomposition conditions including a temperature of about 100° to about 200° C., a pressure of about 80 to about 500 psia at a flow rate of about 0.5 to 20 volumes of feedstock per reactor volume per hour and decomposing peroxide contaminants therein to prepare a tertiary butyl alcohol charge stock comprising about 95 to about 99 wt. % of tertiary butyl alcohol, less than about 0.1 wt. % of peroxide contaminants and from about 0.1 to about 1 wt. % of acidic by-products;

b) continuously charging said charge stock to a tertiary butyl alcohol dehydration reactor operated under reaction conditions including a temperature of about 160° to about 240° C., a pressure of about 80 to about 500 psia at a flow rate of about 0.5 to 20 volumes of charge stock per reactor volume per hour to dehydrate the tertiary butyl alcohol therein to form isobutylene and water and to substantially completely decompose acidic by-products to form a non-corrosive isobutylene feedstock comprising tertiary butyl alcohol, isobutylene and water that is substantially completely free from peroxide and formate contaminants;

c) continuously charging said feedstock to a first distillation column operated under distillation conditions including a liquid reflux temperature of about 30° to about 100° C., a reboiler temperature of about 80° to about 115° C., and a pressure of about 15 to about 60 psia, and separating it therein into a first higher boiling fraction comprising tertiary butyl alcohol and water and a first lower boiling fraction comprising isobutylene and water;

d) continuously recovering isobutylene from the first lower boiling fraction;

e) continuously charging a reaction feed mixture comprising methanol and said recovered isobutylene to an etherification reactor containing a bed of an etherification catalyst operated under reaction conditions including a pressure of about 30 to about 500 psia, a temperature of about 30° to about 200° C., and reacting said reaction feed mixture therein to form a non-corrosive etherification reaction product comprising unreacted methanol, water, isobutylene and methyl tertiary butyl ether; and f) recovering methyl tertiary butyl ether from said reaction product.

11. A method as in claim 10 wherein:

distillation conditions used in the first distillation column include a liquid reflux temperature of about 40° to about 80° C., and a reboiler temperature of about 95° to about 105° C.;

the etherification reactor is operated under reaction conditions including a temperature of 40° to about 90° C., a pressure of about 150 to about 250 psia.

12. A method as in claim 10 including the additional steps of:

g) continuously charging the etherification reaction product to a methanol solvent extraction zone operated under extraction conditions including a temperature of about 20° to about 60° C., and a pressure of about 50 to about 500 psia, and contacting the reacting product therein with water in the ratio of isobutylene to water of about 0.8 to about 1.8 volumes of isobutylene per volume of water per hour to provide an overhead extract comprising isobutylene, water and methyl tertiary butyl ether, and a raffinate comprising methyl tertiary butyl ether, methanol, and water;

h) continuously charging the extract to a second distillation column operated under conditions including a liquid reflux temperature of about 30° to about 60° C., a reboiler temperature of about 100° to about 140° C., and a pressure of about 70 to about 120 psia, and separating it therein into a second lower boiling distillation fraction comprising isobutylene and water and a second higher boiling distillation fraction comprising methyl tertiary butyl ether; and i) continuously recovering isobutylene from said second lower boiling distillation fraction and charging said recovered isobutylene to said etherification reactor.

13. A method as in claim 12 wherein:

extraction conditions include a temperature of about 30° to about 40° C., and a pressure of about 50 to about 150 psia; and the second distillation column is operated under conditions including a liquid reflux temperature of about 40° to about 55° C., a reboiler temperature of about 125° to about 135° C. and a pressure of about 70 to about 120 psia.

14. A method as in claim 10 including the additional steps of:

j) continuously charging the first higher boiling distillation fraction to a third tertiary butyl alcohol recovery distillation zone operated under distillation conditions including a liquid reflux temperature of about 35° to about 170° C., and a reboiler temperature of about 100° to about 190° C., and at a pressure of about 15 to about 190 psia and separating it therein into a third lower boiling tertiary butyl alcohol recycle fraction and a third higher boiling water fraction; and k) continuously recycling the third lower boiling tertiary butyl alcohol fraction to the tertiary butyl alcohol dehydration reactor.

15. A method as in claim 14 wherein the third tertiary butyl alcohol recovery distillation zone is operated under distillation conditions including a liquid reflux temperature of about 140° to about 15° C., a reboiler temperature of about 170° to about 180° C., and at a pressure of about 110 to about 160 psia.

16. A method as in claim 14 wherein an aqueous alkaline solution of an alkali selected from the group consisting of sodium hydroxide, sodium carbonate, and potassium hydroxide is added to the first higher boiling distillation fraction, the alkaline solution being added in an amount sufficient to substantially completely neutralize the acidic by-products present in the first higher boiling distillation fraction.

* * * * *